(12) United States Patent
Junker et al.

(10) Patent No.: US 6,492,327 B2
(45) Date of Patent: Dec. 10, 2002

(54) ISOLATION OF PURIFIED TGF-β1 AND TGF-β2 FROM BONE TISSUE

(75) Inventors: Louis Junker, Erie; Michael Lewis, Englewood; Robert Nelson, Arvada, all of CO (US)

(73) Assignee: Sulzer Biologics Inc., Austin, TX (US)

( * ) Notice: Subject to any disclaimer, the term of this patent is extended or adjusted under 35 U.S.C. 154(b) by 0 days.

(21) Appl. No.: 09/742,681

(22) Filed: Dec. 19, 2000

(65) Prior Publication Data

US 2002/0119539 A1 Aug. 29, 2002

(51) Int. Cl.$^7$ ............... A01N 37/18; A61K 38/00; C07K 1/00; A61F 2/02; A61F 2/00
(52) U.S. Cl. ............... 514/2; 514/12; 514/21; 530/324; 530/841; 424/85.1; 523/115; 623/11; 623/16
(58) Field of Search ............... 530/350, 399, 530/414, 416, 417, 840; 514/2, 21, 801; 523/115; 623/11, 16

(56) References Cited

U.S. PATENT DOCUMENTS

| | | | | |
|---|---|---|---|---|
| 4,002,602 A | * | 1/1977 | Goldstein | 260/112.5 R |
| 4,434,094 A | | 2/1984 | Seyedin et al. | 260/112 |
| 4,627,982 A | | 12/1986 | Seyedin et al. | 424/95 |
| 4,774,228 A | * | 9/1988 | Seyedin et al. | 514/21 |
| 4,789,663 A | | 12/1988 | Wallace et al. | 514/21 |
| 4,795,467 A | | 1/1989 | Piez et al. | 623/16 |
| 4,804,744 A | | 2/1989 | Sen | 530/350 |
| 4,863,732 A | | 9/1989 | Nathan et al. | 424/95 |
| 5,290,763 A | | 3/1994 | Poser et al. | 514/21 |
| 5,322,933 A | * | 6/1994 | Davies et al. | 530/399 |
| 5,371,191 A | * | 12/1994 | Poser et al. | 530/350 |
| 5,563,124 A | | 10/1996 | Damien et al. | 514/21 |
| RE35,694 E | | 12/1997 | Seyedin et al. | 514/2 |
| 5,821,333 A | * | 10/1998 | Carter et al. | 530/350 |
| 6,010,698 A | * | 1/2000 | Kussendrager et al. | 424/94.1 |

OTHER PUBLICATIONS

Farooqui, *Journal of Chromatography*, 184, 335–345, 1980.
Ogawa et al., *The Journal of Biological Chemistry*, 267:4, 2325–2328, 1992.
Seyedin et al., *The Journal of Biological Chemistry*, 262:5, Feb. 15, 1987.
Assoian RK et al., *J Biol Chem*, 258:11, 7155–60 Jun. 10, 1993.
Ogawa, *Methods Enzymol*, 198: 317–27, 1991.
Ogawa et al., *J Biol Chem*, 267:4, 2325–8, May 5, 1992.
Roberts et al., *Biochemistry*, 22:25, 5692–8, Dec. 6, 1983.
Schlunegger et al., *FEBS Lett*, 303:1, 91–3, May 25, 1992.
Seyedin et al., *Proc. Natl. Acad. Sci USA*, 82:8, 2267–71, Apr. 1985.

* cited by examiner

*Primary Examiner*—Jeffrey Fredman
*Assistant Examiner*—Arun Kr. Chakrabarti (57) ABSTRACT

A method for purifying bone-derived TGF-β proteins including an anion exchange process, a cation exchange process, and a reverse phase HPLC process, and optionally, a filtration process, a Heparin-Sepharose process, and/or a reverse phase HPLC desalting process. The filtration process preferably selects proteins having a nominal molecular weight between approximately 10 kilodaltons and approximately 100 kilodaltons. Preferably, the anion exchange process uses a strongly cationic resin having quaternary amine functional groups. Preferably, the cation exchange process uses a strongly anionic resin having sulfonic acid functional groups. The TGF-β proteins can be eluted from the reverse phase HPLC column with an acetonitrile solution in combination with aqueous trifluoracetic acid. The purification processes yield highly enriched TGF-β1 and TGF-β2 proteins.

28 Claims, 7 Drawing Sheets

FIG. 2
Purification of TGF-β1 and TGF-β2 HPLC Chromatogram

FIG. 3

Purification of TGF-β2 Using Heparin Sepharose Chromatography

| | | | |
|---|---|---|---|
| Sample Name | PD#2 TGFb2 Scout | Date Acquired | 2/11/2000 1:09:28 PM |
| Injection Volume | 100.00 µl | Acq Method Set | 0%B step 13%B step 100%B |
| Channel Description | Abs 280 | | |
| Run Time | 50.0 Minutes | Processing Method | Ultra Sensitive |
| Project Name | Heparin | Method Version | **** |
| | | Date Processed | 2/11/2000 2:44:30 PM |

Auto-Scaled Chromatogram

FIG. 4

Purification of TGF-β1 Using Heparin Sepharose Chromatography

FIG. 5
Purification of TGF-β1 and TGF-β2 Multiple Injection Desalting Chromatogram FIG. 6
Purification of TGF-β1 and TGF-β2 HPLC Fraction Gel

FIG. 7
Purification of TGF-β1 and TGF-β2

ISOLATION OF PURIFIED TGF-β1 AND TGF-β2 FROM BONE TISSUE

FIELD OF THE INVENTION

The present invention relates generally to methods for production of transforming growth factor β (TGF-β) and, more particularly, to methods for purification of transforming growth factor β from mammalian bone tissue.

BACKGROUND OF THE INVENTION

Transforming growth factor β (TGF-β) proteins are multi-functional cytokines active in regulating growth, differentiation, and morphogenesis in a wide variety of both normal and neoplastic cell types. These growth factors share related biological activities such as chemotactic attraction of cells, promoting cell differentiation and cartilage- and bone-growth induction. TGF-β is a 25,000 MW homodimer consisting of two 12,500 subunits bound together by nine disulphide bridges. There are three potential N-linked glycosylation sites in the precursor portion of the protein, all of which appear to be used. At least five different forms of TGF-β (TGF-β 1 to TGF-β 5) have been identified and the sequence homology between the different forms of the mature TGF-β peptides range from 64–82%. The sequence homology between the precursor sequences is somewhat lower, averaging about 40%. All are functionally homologous although there is some difference in TGF-β receptor binding properties. TGF-β has been shown to be an effective cell growth promoter, particularly with epithelial cells, and the use of TGF-β as a wound healing agent has been demonstrated. It would therefore be desirable to provide methods for producing TGF-β in relatively large quantities. It would be particularly desirable to provide methods for the purification of TGF-β from mammalian tissue.

Bones include many proteins, some of which induce or promote bone growth. A great deal of research has been directed to producing specific osteoinductive proteins primarily by recombinant DNA techniques or by purification of the naturally occurring proteins. Such proteins and a variety of processes for obtaining them are the subject of numerous patents. However, very little work has been directed to the economic, large scale commercial production of the naturally occuring protein.

Collagen Corporation of Palo Alto, Calif. is the assignee of a number of patents directed to osteoinductive proteins. U.S. Pat. No. 4,434,094 by Seyedin et al., issued Feb. 28, 1984 identifies a process to partially purify an osteogenic factor and isolate a non-fibrous protein having a molecular weight less than 30 kilodaltons (kD) from demineralized bone extract using cation exchange chromatography. A partially purified bone-inducing factor of 10 to 30 kD and the purification process including extraction from demineralized bone, gel filtration, and cation exchange chromatography on a carboxymethyl cellulose column, and which may include reverse phase-high performance liquid chromatography (HPLC), is described in U.S. Pat. No. 4,627,982 by Seyedin et al., issued Dec. 9, 1986. Also by Seyedin et al., U.S. Pat. No. 4,774,228 issued Sep. 27, 1988, describes two 26 kD proteins found in bone having activity in a TGF-β assay and purified using a process similar to that taught in Seyedin's '094 patent but including reverse phase HPLC or acetic acid-urea gel electrophoresis, where the purified proteins exhibit chondrogenic activity (purportedly related to bone formation). U.S. Pat. No. 4,863,732 by Nathan et al., issued Sep. 5, 1989 is directed to an injectable solution of an osteogenic factor such as that described in Seyedin's '982 patent, combined with atelopeptide collagen and further purified by coprecipitation. Other patents relate to mixtures of atelopeptide collagen material, e.g. U.S. Pat. No. 4,789,663 by Wallace et al., issued Dec. 6, 1988 and U.S. Pat. No. 4,795,467 by Piez et al. issued Jan. 3, 1989.

U.S. Pat. No. 4,804,744 by Sen, issued Feb. 14, 1989 identifies a primary osteogenic protein ($P_3$) with a molecular weight of about 22 to 24 kD. This patent also identifies proteins $P_2$ and $P_4$ which are nonosteogenic without $P_3$, and further identifies a method for isolating $P_3$ from demineralized bone tissue including extraction, dialysis, gel filtration and HPLC steps.

U.S. Pat. Nos. 5,290,763, 5371,191 and 5,563,124 to Poser et al., Poser et al., and Damien et al. respectively describe isolation of a growth factor mixture by a multi-step procedure which preferably includes preparing the bone for extraction of proteins by grinding, cleaning, and demineralizing the bone, extracting the bone proteins, and concentrating the extracted proteins by multiple purification steps.

There is a need for a process to efficiently isolate TGF-β proteins from a natural source on a commercial scale. It would also be beneficial if such proteins could be produced in a manner designed to minimize degradation of such proteins while maximizing production. It would also be beneficial if such proteins could be produced using relatively well-known unit operations in a process which is tolerant of minor variations in process conditions.

SUMMARY OF THE INVENTION

One embodiment of the present invention is a process for purifying TGF-β proteins from a first solution that contains demineralized bone extract. The process includes subjecting the first solution to filtration to obtain a second solution containing proteins having a desired range of molecular weights, for example between nominal molecular weight cutoffs of 10 kD and 100 kD. The pH of the second solution can be from about pH 8 to about pH 9. The second solution is loaded onto an anion exchange resin and the void volume is collected. The anion exchange resin can include quaternary amine functional groups. The pH of the void volume is from about pH 8.0 to about pH 9.0, more preferably about pH 8.3 to about pH 8.7, and more preferably about pH 8.4 to about pH 8.6. The void volume is loaded onto a cation exchange resin and a protein fraction is eluted from the cation exchange resin with a first eluant to obtain a cation exchanged fraction eluate. The cation exchange resin can include sulfonic acid functional groups. The process next includes loading the cation exchanged fraction eluate onto a reverse phase HPLC column and eluting protein fractions from the HPLC column to obtain HPLC fraction eluates enriched in either TGF-β1 or TGF-β2 proteins. The HPLC column can be either a plastic or hydrocarbon-modified silica packing.

The process can also include a further step of loading the HPLC fraction eluate onto a Heparin-Sepharose column; and eluting a protein fraction from the Heparin-Sepharose column to obtain an Heparin-Sepharose eluate enriched in either TGF-β1 or TGF-β2 proteins. The process can further include a step of loading the Heparin-Sepharose eluate onto a reverse phase HPLC column to desalt the protein product. A further process step can include dialyzing the cation enchanged fraction eluate into deionized water using a 3.5 kD molecular weight cut off ("MWCO") dialysis membrane.

In a preferred embodiment: the conductivity of the anion exchange load solution (also referred to herein as the "second solution") is adjusted, if necessary, to a conductivity of less than about 1,300 μmhos ($1300 \times 10^{-3}$ S) prior to loading onto the anion exchange resin. The void fraction is not retained by the column and has a conductivity in a range from about 900 μmhos (900 uS) to about 1300 μmhos (1300 u S); In another preferred embodiment, the step of eluting a protein fraction from the HPLC column to obtain a HPLC fraction eluate comprises eluting a protein fraction from the HPLC column with a second eluant having a gradient of increasing acetonitrile concentration ranging from about 25 percent by volume to about 60 percent by volume to obtain a purified protein mixture. More particularly, the step of eluting a protein fraction from the HPLC column can include collecting aliquots eluting at approximately 36 percent by volume acetonitrile to produce a TGF-β1 fraction and/or can include collecting aliquots eluting at approximately 39 percent by volume acetonitrile to produce a TGF-β2 fraction.

Further embodiments of the present invention include compositions which include TGF-β protein produced by processes of the present invention, and more particularly compositions which include TGF-β1 and/or TGF-β2 proteins produced by processes described herein.

DETAILED DESCRIPTION OF THE INVENTION

In one embodiment of the present invention, the process for purifying TGF-β proteins from demineralized bone extract includes size filtration steps, an anion exchange chromatography step, a cation exchange chromatography step, and a high performance liquid chromatography (HPLC) step. Further embodiments can include a Heparin-Sepharose purification step and/or a final HPLC desalting step. Another embodiment of the invention is the resulting TGF-β1 and TGF-β2 protein compositions. A preferred starting material for the present process is a demineralized bone extract which can be obtained by a multi-step procedure which preferably includes preparing the bone for extraction of proteins by grinding, cleaning, and demineralizing the bone. The process then includes extracting the bone proteins and concentrating the extracted proteins with multiple purification steps. The preferred source of starting material for the present process is mammalian bone. Because of its ready availability and low costs, bovine bone is typically used. Other mammalian bone, however, can be suitable for practicing the invention. The bone is prepared for extraction of bone proteins by customary means known in the art, such as removing all soft tissue and then grinding the bone. Following the cleaning of individual segments the bone is ground into successively finer particles in preparation for demineralization. Preferably the bone is ground to particles less than 4 mm in size and preferably from about 0.3 mm to about 3 mm in size The cleaned ground bone is then demineralized with acid. The bone is soaked in any suitable acid and may be agitated, preferably at room temperature. The pH of the acid soaking solution typically is maintained at or below pH 1.3. A solution of dilute HCl (e.g. from about 0.6 M to about 1.2 M) is effective to demineralize bone. Alternatively other suitable acids such as formic acid can be used. Octyl alcohol or other defoaming agents are useful to prevent excessive foaming during demineralization.

The bone is soaked in acid for sufficient time until the bone is substantially completely demineralized. X-ray analysis may be used to evaluate the extent of demineralization. Alternatively, standard procedures can be developed through experience to determine the amount of time required for demineralization including the high temperature washing of the demineralized bone particles and subsequent measurement of residual calcium and phosphate. Typically, at least seven to twelve hours is required. The demineralized bone is then rinsed to remove the acid. Typically the bone is rinsed with water overnight or until the pH of the rinse discharge reaches pH 4 or more. As will be appreciated by those skilled in the art, alternative cleaning and demineralizing processes can also be employed.

Proteins are extracted from the demineralized bone using a protein denaturant such as guanidine and/or urea. In one embodiment preferably the extraction is performed at less than 20° C. and more preferably at less than 15° C. It should be noted that other suitable denaturants can be used as well. In another embodiment the bone protein extraction can be performed at room temperature. Guanidine hydrochloride is a preferred denaturant because it is ionic and therefore also functions well as a solubilizing agent for maintaining proteins in solution. A 4M guanidine, 100 mM tris [hydroxymethyl]aminomethane (tris), pH 7.4, solution is a preferred extraction solution. Higher concentrations of guanidine hydrochloride can also be used in the extraction buffer (6 M guanidine, 100 mM tris[hydroxymethyl] aminomethane (tris), pH 7.4) Optionally, a specialized column that circulates the extraction solution through a fluidized bed of the demineralized bone matrix can be used to extract proteins from bone.

Optionally, a chaotrope can be added during extraction to improve solubility of extracted proteins. Suitable chaotropes include calcium chloride ($CaCl_2$), magnesium chloride ($MgCl_2$), and cesium chloride ($CeCl_2$).

Protein can be extracted from demineralized bone by means typically used in the art. For example, a protein denaturant can be pumped through demineralized bone in a filter press to extract proteins in recovered denaturant. In order to provide appropriate low temperatures, the denaturant can be cooled to an initially low temperature, preferably from about 0° C. to about 4° C., as it is pumped through the demineralized bone. The temperature of the denaturant can increase during the extraction process. Optionally, a specialized column that circulates the extraction solution through a fluidized bed of the demineralized bone matrix can be used to extract proteins from bone.

Usually, extraction continues until substantially all of the noncollagenous bone proteins have been removed from the demineralized bone. A typical extraction takes about 40 to 72 hours. Preferably the extraction solution is maintained near neutral pH. Proteins in the demineralized bone extract solution are then separated by a series of filtration steps to remove proteins smaller than 10 kD and larger than 100 kD. Preferably, as a first step, the extract solution is subjected to a filtration step in which proteins larger than 100 kD are removed. In a preferred embodiment, this step is performed in a Sartorius tangential flow filtration apparatus using a 100 kD nominal molecular weight cutoff filter cassette (such as Sartorius Sartocon® modified polysulfone membrane cassette, 0.7 $m^2$ each, 8 cassettes, with total membrane equaling 5.6 $m^2$). The filtration can be conducted under pressure and typically at about 50 psi filtration pressure. The protein concentration will vary depending on the completeness of the extraction.

The permeate from this filtration step is then subjected to a second filtration step in which proteins smaller than 10 kD are removed. In a preferred embodiment, this step is performed in a Sartorius tangential flow filtration apparatus using a 10 kD nominal molecular weight cutoff filter cassette (such as Sartorius Sartocon® membrane cassette, 0.7 $m^2$ each, 8 cassettes, with total membrane equaling 5.6 $m^2$). The filtration can be conducted under pressure and typically at about 50 psi filtration pressure. The protein concentration will vary depending on the completeness of the extraction. The second filtration yields a retentate with a mixture of proteins having molecular weights within a desired range ("filtered protein concentrate").

In preparation for subsequent ion exchange chromatography, the filtered protein concentrate can be transferred from an ionic denaturant solution to a non-ionic denaturant solution, such as urea. A non-ionic denaturant is preferred for use in the subsequent ion exchange purification steps because an ionic denaturant, such as guanidine hydrochloride, impairs the ability of the ion exchange resins to selectively bind desired proteins. For example, the filtered protein concentrate is diafiltered into a 20 mM tris, 6 M urea having a pH of about 8.5, using about 8–10 volumes of diafiltrate solution. The operation of the step is continued until the conductivity of the retentate solution approaches the conductivity of the diafiltrate solution (less than 1300 micromhos ($1.3 \times 10^{-3}$ S)). Through the use of diafiltration or dialysis the filtered protein concentrate can be transferred to the appropriate denaturant without precipitation of proteins from solution. This procedure is advantageous because it simplifies subsequent purification and prevents losses that can occur if proteins are allowed to precipitate. It is also advantageous that this procedure can be used on a commercial production scale.

The present invention includes an anion exchange process to purify a solution of extracted bone proteins to yield highly purified TGF-β proteins. In a preferred embodiment of the anion exchange process, the starting material is prepared using the above-described process for obtaining a preferred starting material. The anion exchange process is combined with additional purification processes described below.

In ion exchange chromatography, i.e., anion exchange and cation exchange chromatography, the affinity of a particular protein for a particular ion exchange resin depends on the ionic strength of the protein solution and pH. The ionic strength of a solution can be measured by its conductivity. Alternatively, the ionic strength of a solution can be measured in terms of a specific counterion concentration. As used herein, the term "counterion concentration" refers to the molar concentration of an ion in solution which competes with proteins for binding sites on the ion exchange resin.

Prior to loading the filtered protein concentrate solution onto an anion exchange column in accordance with the present invention, the conductivity of the protein solution is adjusted to allow the desired proteins to bind selectively to the resin. In the present anion exchange process, the protein solution can be 6 M urea, 20 mM Tris, and the conductivity of the solution can be adjusted to less than about 1,300 μmhos ($1.3 \times 10^{-3}$ S), and in an alternative embodiment from about 900 μmhos ($0.9 \times 10^{-3}$ S) to about 1,900 μmhos ($1.9 \times 10^{-3}$ S) by variation in the counterion concentration. The protein solution to be purified by the anion exchange process, having an appropriate conductivity, is loaded onto an anion exchange column and the void volume comprising TGF-β proteins is collected for further processing. In the present anion exchange process, the anion exchange column has a strongly positive anion exchange resin inside the column. It has been found that the present anion exchange process with a strongly positive anion exchange resin is effective in purifying a mixture of proteins including TGF-β1 and TGF-β2. As used herein, the term strongly positive anion exchange resin refers to a resin having strongly positive functional groups such as quaternary amine functional groups. A preferred resin with quaternary amine functional groups is Q-Sepharose fast flow® (from Pharmacia). However, other resins having similarly basic functional groups are suitable as well.

A further factor affecting the selectivity of binding to the anion exchange resin is the pH of the protein solution being loaded onto the anion exchange column. The pH of the protein solution is at a pH effective to allow the resin to bind desired proteins from the protein solution as it passes through the column and to allow for desired passage of proteins in the void volume. Generally, a pH of between about pH 8 and about pH 9 is effective in the present process. Preferably, the pH of the protein solution is adjusted to about pH8.5.

The linear velocity of the protein solution through the anion exchange column is determined by required recovery parameters. Typically, the process is run at a low velocity (approximately 30 cm/hr) to allow for substantially complete adsorption of desired proteins so that passage of undesired protein in the void volume is minimized. It should be recognized, however, that the linear velocity can be greater, but that protein profile of the void volume may be sustained.

It should be noted that while the present invention is directed to the preparation of a TGF-β protein composition from the void volume of the anion exchange process, the proteins which are bound to the anion exchange resin are also biologically active proteins. Such bound proteins can be eluted and recovered for use. For example, as shown in U.S. Pat. No. 5,371,191, such proteins can recovered and further processed to make an osteoinductive protein composition.

After loading the bone protein solution onto the anion exchange column, the void volume is a fraction of proteins that is not retained by the column (the void fraction). This fraction is a mixture of very basic proteins (proteins with isoelectric points above 7) and is particularly enriched in TGF-β1 and TGF-β2 proteins. This void fraction is retained for further purification of TGF-β1 and TGF-β2 proteins.

The void fraction from the anion exchange chromatography can be further processed into an appropriate solution for cation exchange chromatography. In the present invention, the void fraction can be first concentrated and then diafiltered with a tangential flow filter into the desired solution. In a preferred embodiment, the void fraction is concentrated to reduce the volume by 90% with a Millipore Pellicon-2® mini modified polyethersulfone filter (0.1 $m^2$ surface area, 3 cassettes, total surface area=0.3 m²) having a nominal molecular weight cut off of 5 kD. The retentate is then diafiltered using a solution of 6 M urea, 50 mM sodium acetate, 10 mM sodium chloride, and 1% by volume isopropanol, pH 4.6) in 8 to 10 volumes of buffer. Following diafiltration, the protein solution is ready to be purified by cation exchange chromatography.

The present invention includes a cation exchange chromatography process to further purify TGF-β1 and TGF-β2 proteins from bone-derived proteins in solution which may be used advantageously in combination with the anion exchange process described above and the HPLC process described below.

As discussed above with respect to the anion exchange process, the conductivity of the protein solution being applied to the cation exchange resin is controlled to effect selective binding of proteins to the resin. Prior to loading the protein solution onto a cation exchange column in the present invention, the conductivity of the protein solution is adjusted to be effective to allow the cation exchange resin to selectively bind a desired fraction of proteins. In the present cation exchange process, the conductivity of the protein solution is preferably from about 1000 μmhos ($1.00\times10^{-3}$ S) to about 2000 μmhos ($2.0\times10^{-3}$ S). and more preferably below 1500 μmhos ($1.5\times10^{-3}$ S). In a preferred embodiment, the counterion concentration of the protein solution applied to the cation exchange resin is about 10 mM NaCl in a buffer containing 50 mM sodium acetate, 6 M urea, 1% IPA and a pH of 4.6.

The protein solution to be purified by the cation exchange, having an appropriate conductivity, is loaded onto a cation exchange column. In the present cation exchange process, a strongly negative cation exchange resin has been found effective in purifying a mixture of the TGF-β1 and TGF-β2 proteins. As used herein, the term strongly negative cation exchange resin refers to a resin having strongly negative functional groups such as sulfonic acid functional groups. A preferred resin with sulfonic acid functional groups is SP-Sepharose® (from Pharmacia). However, other resins having similarly acidic functional groups are suitable as well.

The pH of the protein solution to be purified by the cation exchange process is adjusted to be a pH for effective binding of desired proteins to the resin. In the present process, a pH of between about pH 4.2 and about pH 5.0 is preferably used. Preferably the pH of the protein solution is adjusted to about pH 4.6.

The linear velocity of the bone protein solution through the cation exchange column, as with the anion exchange above, is determined by required recovery parameters. The velocity (18–30 cm/hr) is generally sufficiently low to permit substantially complete adsorption of the desired proteins with minimal protein loss.

The cation exchange process further includes selectively desorbing desired fraction of bound proteins from the column resin. Proteins are eluted from the cation exchange column with an eluant having a conductivity suitable to yield TGF-β1 and TGF-β2 protein mixtures. For the present cation exchange process, proteins are eluted from the cation exchange column using a NaCl gradient. The gradient used is one where the concentration of NaCl is varied from 10 mM to 600 mM in approximately 7 column volumes of buffer (50 mM sodium acetate, 6 M urea, 1% IPA, pH 4.6). The conductivity of the eluant varies from 1500 μmhos ($1.5\times10^{-3}$ S) to about 40,000 μmhos ($4.0\times10^{-2}$ S).

Generally, the eluant for the present process is a solution having a suitable protein denaturant, such as urea, and an appropriate salt concentration to achieve the desired conductivity. In a preferred embodiment, the eluant is prepared with a counterion concentration from about 0.01 M NaCl to about 0.6 M NaCl, more preferably from about 0.3 M to about 0.6 M NaCl, and more preferably 0.4 to 0.55 M NaCl to provide the appropriate conductivity. One preferred eluant is prepared by combining 6 M urea, 50 mM sodium acetate, 10 mM sodium chloride, 1% isopropanol by volume, pH 4.6 with 6 M urea, 50 mM sodium acetate, 600 mM sodium chloride, 1% isopropanol by volume, pH 4.6 in a linear gradient. The TGF-β1 and TGF-β2 proteins eluate at a sodium chloride concentration of about 0.3 M to about 0.6 M and more specifically, 0.4 to 0.55 M NaCl.

The protein eluate from the cation exchange chromatography column is then dialyzed prior to further purification via HPLC. In one embodiment, the protein eluate is dialyzed into deionized water using a 3.5 kD molecular weight cut off dialysis membrane. The dialyzed proteins are then lyophilized and redissolved in 0.1% trifluoroacetic acid. Preferably, the proteins are redissolved at a concentration of 10–15 mg/ml prior to purification on a HPLC column.

The present invention further includes a reverse phase HPLC process which may be combined with the anion and cation exchange processes described above to separate and further purify the TGF-β1 and TGF-β2 proteins. In the HPLC purification process of the present invention, a protein solution is loaded onto a reverse phase HPLC column. This column may be polymeric (e.g., polystyrene) or silica based. Preferably, the HPLC column is a hydrocarbon modified silica. Preferably, a silica resin is modified by the addition of $C_4$–$C_{18}$ hydrocarbon chains, and more preferably, the HPLC column is a VYDAC® $C_{18}$ column.

The protein solution to be loaded onto the reverse phase column can be a solution of trifluoroacetic acid or other suitable solvent (e.g. heptafluorobutyric acid or phosphoric acid). Preferably, a trifluoroacetic acid solution is used having a concentration of from about 0.05 percent by volume to about 0.15 percent by volume, and more preferably about 0.1 percent by volume trifluoroacetic acid.

TGF-β1 and TGF-β2 proteins are selectively eluted from the HPLC column with an organic solvent/water/trifluoroacetic acid mixture suitable for obtaining the desired proteins. A preferred eluant in the HPLC process is an acetonitrile solution. The preferred eluant typically has an acetonitrile concentration which varies, during elution, from about 25 percent by volume to about 60 percent by volume, more preferably from about 25 percent by volume to about 55 percent by volume and more preferably from about 29 percent by volume to about 55 percent by volume. In preferred embodiments, the acetonitrile concentration in the eluant is increased in increments of between about 0.30 percent by volume and about 0.40 percent by volume per minute until the desired highest concentration of acetonitrile is achieved. In this embodiment, HPLC fractions eluting at approximately 35–37% acetonitrile are collected and pooled for further purification and isolation of TGF-β1 proteins and HPLC fractions eluting at approximately 38–40% acetonitrile are collected and pooled for further purification and isolation of TGF-β2 proteins. Preferably, individual aliquots of pooled fractions for each of the TGF-β streams is analyzed by SDS-PAGE and Western Blot analysis after the HPLC purification to verify the presence of TGF-β proteins in the respective fractions. Proteins can be recovered from the HPLC eluant by means generally known in the art.

Following HPLC separation, the fraction containing TGF-β1 and the fraction containing TGF-β2 can be further purified in parallel by identical means. The protein fractions are first transferred into a suitable solution and then separately loaded onto a Heparin-Sepharose column. In the present invention, the respective protein fractions can be lyophilized and then redissolved in 6 M urea, 50 mM potassium phosphate, pH 8.0.

Each protein fraction is loaded separately onto a Heparin-Sepharose column and eluted with a suitable eluting medium having a high ionic strength. In a preferred embodiment for the purification of TGF-β2, the protein is not initially retained by the column and can therefore be found in the column void. In the preferred embodiment for the purification of TGF-β1, a mixture of 6 M urea, 50 mM potassium phosphate, pH 8.0. and a solution of 6 M urea, 50 mM potassium phosphate, 750 mM sodium chloride, pH 8.0 is used to elute the TGF-β1. In this embodiment, TGF-β1 elutes at a sodium chloride concentration range from about 100 mM. The high sodium chloride fraction which elutes following the TGF-β1 fraction is known to contain other growth factors including BMP-2, BMP-3 and BMP-7. Preferably, individual aliquots of pooled fractions from the Heparin-Sepharose columns are analyzed by SDS-PAGE and Western Blot analysis after this purification step to positively identify fractions containing TGF-β1 or TGF-β2 proteins.

Optionally, each protein fraction is subjected to a final HPLC desalting purification step to obtain highly purified TGF-β1 and TGF-β2 proteins.

Further embodiments of the present invention are TGF-β1 and TGF-β2 protein compositions which can be obtained by the various purification processes of the present invention. TGF-β1 and TGF-β2 protein compositions of the present invention are typically at least about 60% of the respective TGF-β protein component, more preferably, at least about 80%, and most preferably, at least about 90%.

A protocol for preparing materials of the present invention is provided below.

1. Starting Material

The starting material for the purification of transforming growth factors 1 and 2 ("TGFβ-1/TGFβ-2") is a side stream from purification of an osteoinductive protein mixture as described U.S. Pat. No. 5,290,763. During operation of the anion exchange ("AX") column, there is a portion of protein that is not retained by the column (termed the "Void"). This protein fraction elutes during the protein loading step and is comprised of very basic proteins (with isoelectric points above pH 7.0) such as TGFβ-1/TGFβ-2. Under current operating conditions for the AX column (protein loaded in 20 mM tris, pH 8.5 in 6 M urea, conductivity 900–1300 μS) the amount of protein in the Void fraction typically represents about 5% of total protein loaded onto this chromatography column. The pH of this fraction should be approximately 8.5 with conductivity equal to the conductivity of the equilibration buffer for the AX step.

2. Concentration and Diafiltration

Non retained protein from the AX column run (AX Void) is obtained from Manufacturing. Typically, the concentration based on absorbance at 280 nm is less that 0.3 mg/ml and volume is approximately 2 column volumes ("cv") or 60 L.

The Void solution is concentrated and diafiltered using a tangential flow filtration apparatus. The apparatus used is an M-12 with three Millipore Pelicon 2 Mini, 5K MWCO, polyether sulfone ("PES"), "A" type screen membranes (0.1 m² each for a total of 0.3 m² of membrane).

Concentration is performed with the M-12 at 50% pump speed and 5 psi backpressure. The initial flux rate is typically 40 ml/min. Due to the large volume the concentration is performed overnight for a total processing time of approximately 24 hours. The protein solution is concentrated until the final volume is 2 L.

The diafiltration step is performed after the concentration step has been completed. Generally, 6–10 volumes of diafiltration buffer is used to completely diafilter the Void protein fraction. The buffer used for the diafiltration step is equilibration buffer for the cation exchange step (50 mM sodium acetate, 10 mM NaCl, 1% isopropyl alcohol ("IPA"), pH 4.6, conductivity approximately 1400 μS). When the diafiltration has been completed, a final concentration is performed to reduce the volume to approximately 1 L.

Typically, overall recovery is very good for these steps (>95%) based on protein absorbance at 280 nm.

3. Cation Exchange

The first major purification step for TGFβ-1/TGFβ-2 is performed using a cation exchange step. Details of the column operation are provided below.

Figure 1:
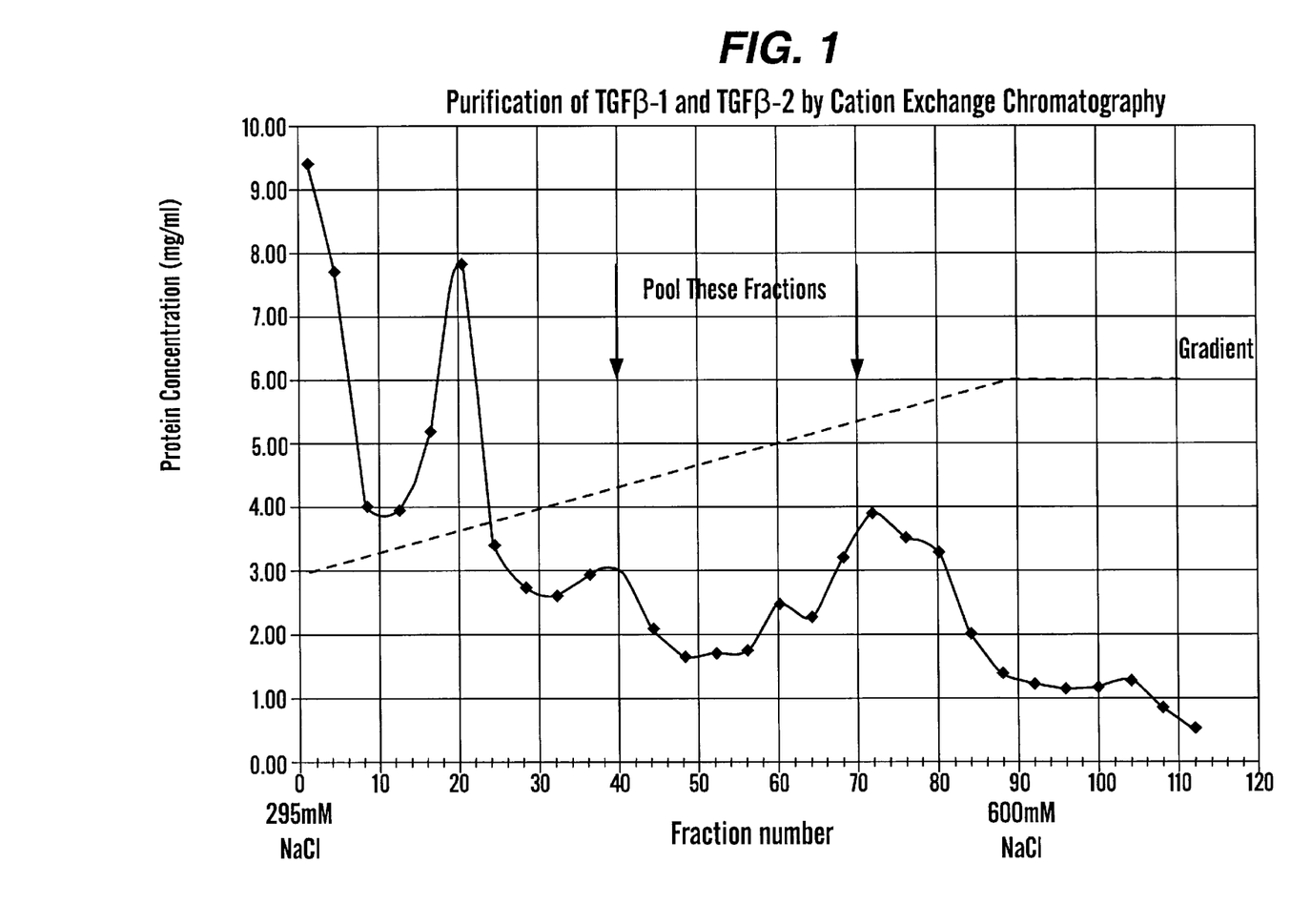
FIG. 1 shows the typical protein elution profile from the cation exchange column.

| Hardware: | |
|---|---|
| Column used: | Pharmacia XK50/30 (diameter of the column is 5 cm) |
| Cross Sectional Area: | Defined as $\pi r^2$ = 19.6 cm² |
| Chromatography Resin: | Pharmacia SP Sepharose fast flow |
| Column Volume: | 26 cm bed height = 510 ml column |
| Controller: | "BioCad" with a fraction collector |
| Column Operation: | |
| Buffers: | |
| Buffer A: | 50 mM sodium acetate, 10 mM NaCl, 6M urea, 1% IPA, pH 4.6, and conductivity approximately 1500 μS. |
| Buffer B: | 50 mM sodium acetate, 600 mM NaCl, 6M urea, 1% IPA, pH 4.6, and conductivity approximately 40 mS |
| Buffer C: | 50 mM sodium acetate, 1.5M NaCl, 6M urea, 1% IPA, pH 4.60, and conductivity approximately 80 mS |
| Equilibration: | 5 cv of Buffer A is used (or until the pH and conductivity of the column effluent match the buffer). Flow rate is approximately 150 ml/min (equivalent to 450 cm/hr). |
| Protein Load: | The protein solution is first filtered through a 0.45 μM membrane filter to remove particulates. The column is then connected to a "BioCad" programmable purification system. The Void fraction is loaded onto the fully equilibrated column at a flow rate of 6–10 ml/min (18–30 cm/hr). The entire 1 L Void fraction is loaded onto the column (representing approximately 2 cv). The concentration of the Void fraction is typically around 10 mg/ml. |
| Post Load Wash: | 1–2 cv Buffer A is used (or until column effluent pH and conductivity reaches that of the buffer). |
| Protein Elution: | Protein is eluted from the column using a buffer gradient from 0% Buffer B to 100% Buffer B in a total volume of 6.8 cv. Part of the elution profile is shown in FIG. 1. TGFβ-1/TGFβ-2 fractions typically elute from 400 to 550 mM NaCl. Protein is collected from the column eluate (20 ml fractions) after 3.4 cv of the elution cycle had passed through the column. Typically, fractions number 110–120. |
| Column Regeneration: | Following the protein elution the column is first cleaned using 3 cv Buffer C. A more rigorous cleaning cycle is performed with the column offline using with 2M NaCl and 1M NaOH. |
| Protein Pooling: | A chromatogram showing the positions of the fractions is generated (FIG. 1). Fractions containing TGFβ-1/TGFβ-2 are identified by a combination of SDS-PAGE analysis and Western Blotting. Pooling of the fractions containing both growth factors is then performed. In general, the |

| | |
|---|---|
| 4. Dialysis/ Lyophilization: | pooled fractions represent 30–20 ml fractions for a total volume of 600 ml. Pooled fractions are exhaustively dialyzed against deionized water in dialysis bags (Spectro/Pro, 3.5 Kd MWCO). Following dialysis, the protein is lyophilized into a dry protein "cake". In preparation for the HPLC purification step the lyophilized protein is dissolved at 10–15 mg/ml in deionized water containing 0.1% trifluoroacetic acid ("TFA"). The total protein at this stage represents 1000–2000 mg (based on absorbance at 280 and an extinction coefficient of 1.0) |

5. HPLC

The second purification step for TGFβ-1/TGFβ-2 is performed using a reverse phase HPLC column. Details of the column operation are provided below. This step results in two separate fractions containing enriched TGFβ-1 and TGFβ-2 proteins

Figure 2:
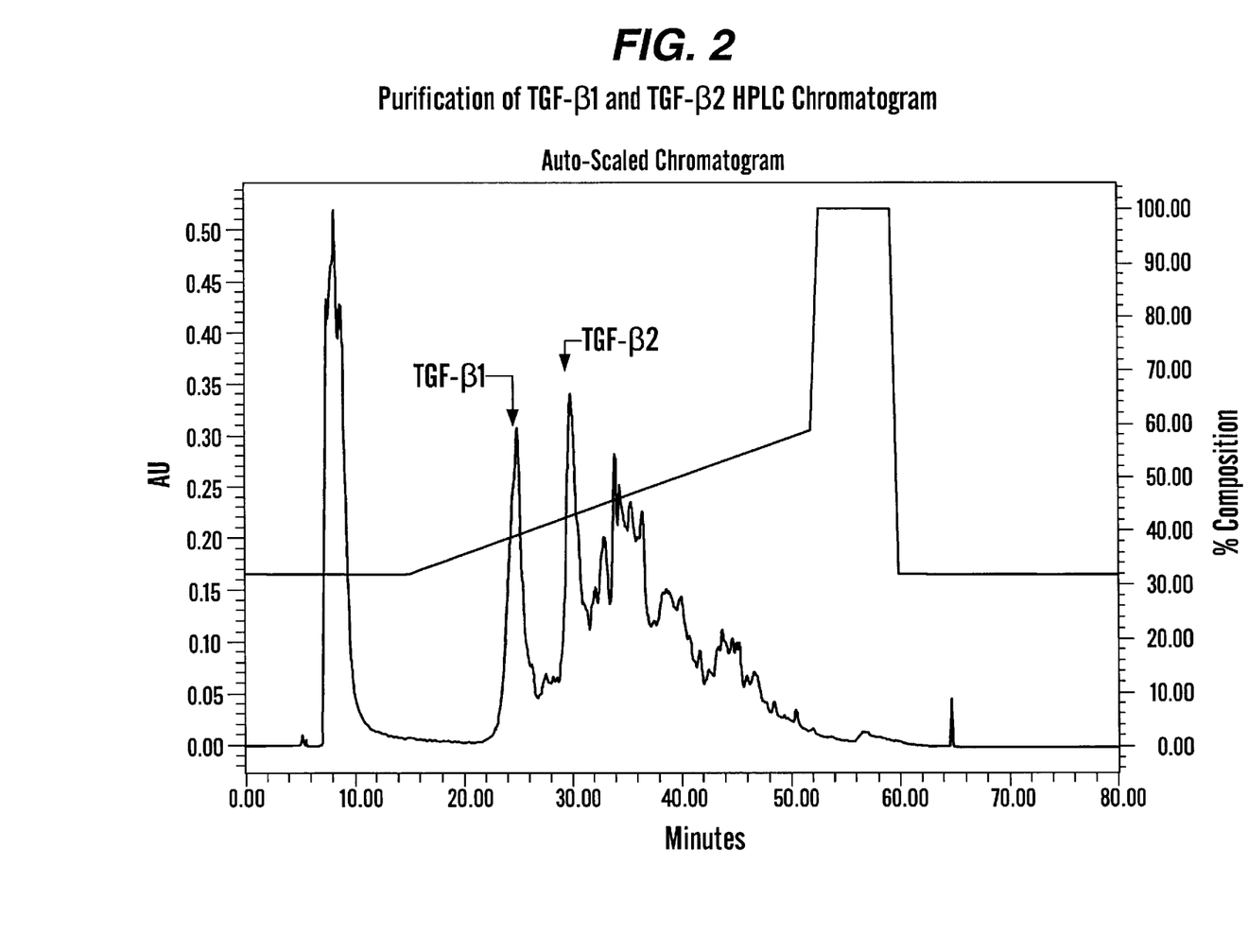
FIG. 2 shows the typical protein elution profile from the reverse phase HPLC column.

| Hardware: | |
|---|---|
| Column used: | Vydac 2.2 cm diameter × 25 cm height column |
| Cross Sectional Area: | Defined as $\pi r^2 = 3.8$ cm$^2$ |
| Chromatography Resin: | 10–15 μM silica beads modified with C-18 groups |
| Column Volume: | 25 cm bed height = 95 ml column |
| Controller: | Waters LC 600 HPLC system with a fraction collector |
| Column Operation: Buffers: | |
| Buffer A: | Deionized water with 0.1% trifluoroacetic acid TFA |
| Buffer B: | 90% acetonitrile ("ACN"), 9.9% deionized water with 0.1% TFA |
| Equilibration: | The column is equilibrated in 3–5 cv of Buffer A:Buffer B (68:32, or about 29% ACN). The flow rate is 11.4 ml/min (equivalent to 180 cm/hr). |
| Protein Load: | The dialyzed CX peak fraction (in 0.1% TFA) is loaded onto the fully equilibrated column at a flow rate of 11.4 ml/min (180 cm/hr). For each run 100–150 mg of total protein is loaded onto the HPLC column. Typically this represents 10–15 ml (at 10–15 mg/ml). Therefore, multiple runs of the HPLC are performed for each purification cycle (5–10 runs). |
| Post Load Wash: | A 2 cv wash is then performed (Buffer A:Buffer B, 68:32, or about 29% ACN) prior to initiation of the elution cycle. |
| Protein Elution: | Protein is eluted from the column using an ACN gradient from 29% (mixed from Buffers A and B described above) to 53% ACN (41:59, Buffer A:Buffer B). The total volume of the gradient represents 4.5 cv. TGF β-1 elutes from 35–37% ACN while TGF β-2 elutes from 38–40% ACN. The elution profile is shown in FIG. 2. Individual fractions are collected every 30 seconds from the column eluate (5.7 ml fractions). Typically 2–4 fractions are pooled for the individual protein pools. |
| Column Regeneration: | Following the protein elution the column is cleaned with 1–2 cv of 100% Buffer B. |
| Protein Pooling: | Fractions containing TGFβ-1/TGFβ-2 are identified by a combination of SDS-PAGE analysis and Western Blotting. Pooling of the fractions containing individual growth factors is then performed. |
| Lyophilization: | Pooled fractions of TGFβ-1 and TGFβ-2 are then lyophilized and redissolved at 1 mg/ml in the equilibration buffer for the Heparin-Sepharose column (Buffer A, see below). |

6. Heparin Sepharose Chromatography

The final major purification step for the TGFβ-1 and TGFβ-2 fractions is performed using a Heparin Sepharose column. Details of the column operation are provided below. Separate TGFβ-1 and TGFβ-2 fractions are purified using this column step.

Figure 3:
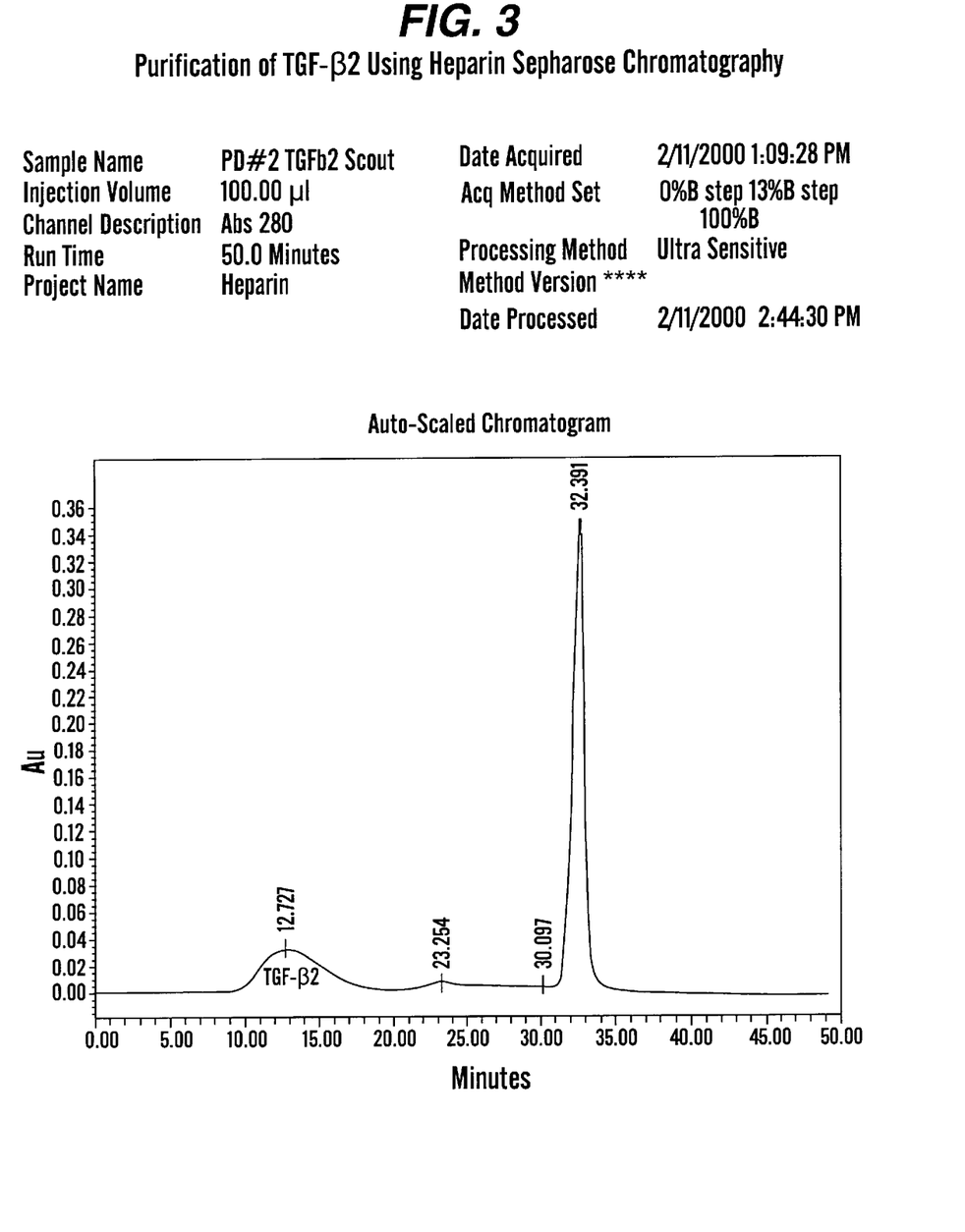
FIG. 3 shows the protein elution profile for TGF-β2 from the Heparin-Sepharose column.
Figure 4:
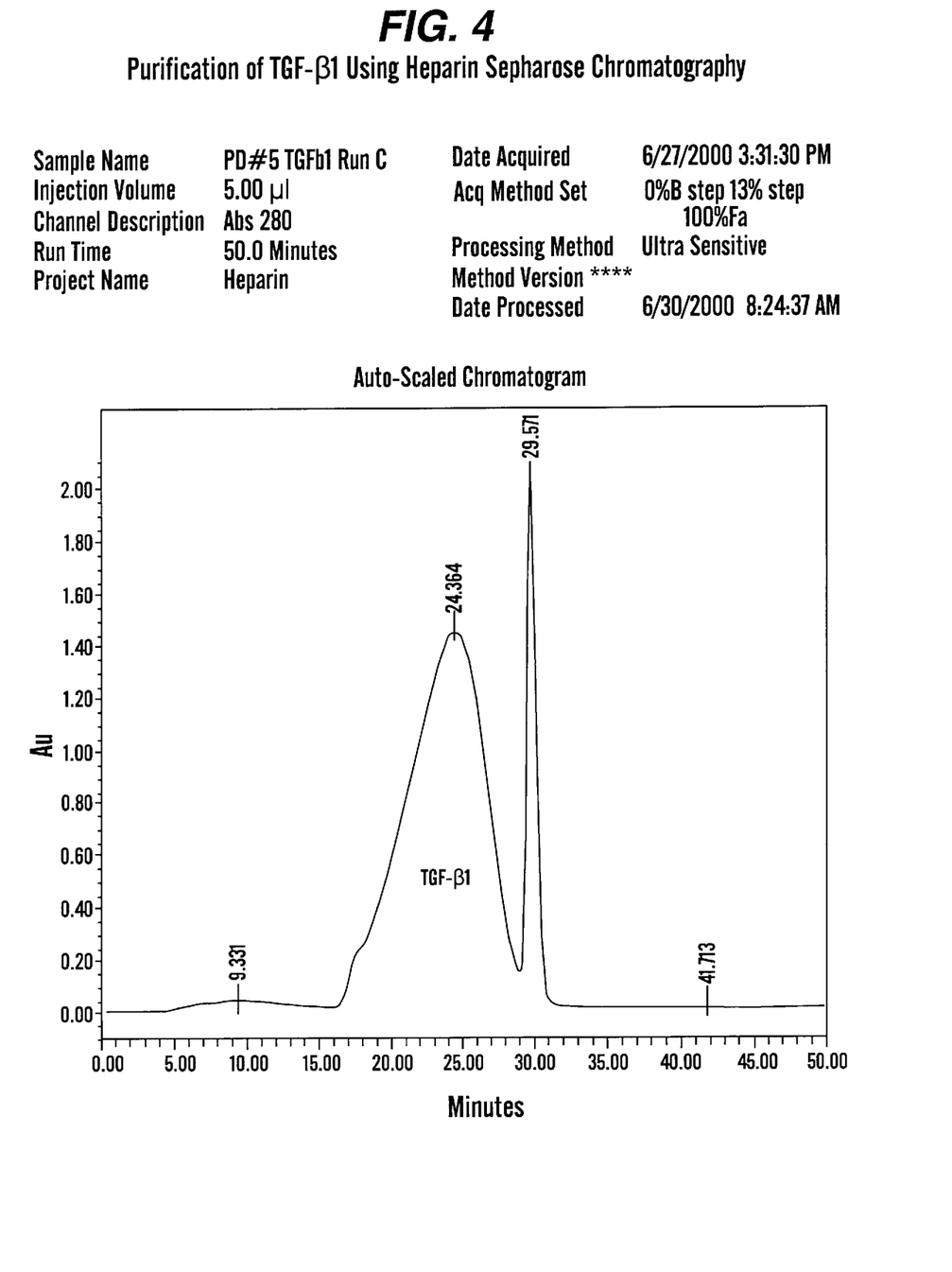
FIG. 4 shows the protein elution profile for TGF-β1 from the Heparin-Sepharose column.

| Hardware: | |
|---|---|
| Column used: | Pharmacia HiTrap column containing high performance Heparin Sepharose resin. Column dimensions are 1.6 cm diameter × 2.5 cm height. |
| Cross Sectional Area: | Defined as $\pi r^2 = 2.0$ cm$^2$ |
| Chromatography Resin: | High performance Heparin Sepharose |
| Column Volume: | 2.5 cm bed height = 5.0 ml column |
| Controller: | Pharmacia AKTA Explorer automated purification system |
| Column Operation: Buffers: | |
| Buffer A: | 50 mM potassium phosphate, 6M urea, pH 8.0 |
| Buffer B: | 50 mM potassium phosphate, 6M urea, 750 mM NaCl, pH 8.0 |
| Equilibration: | The column is equilibrated using 5 cv of Buffer A. The flow rate is 5.0 ml/min (equivalent to 150 cm/hr). |
| Protein Load: | The lyophilized HPLC peak fractions (either TGFβ-1 or TGFβ-2) are loaded onto the fully equilibrated column at a flow rate of 1.0 ml/min (30 cm/hr). The column is loaded with a maximum of 7.5 mg protein (7.5 ml or 1.5 cv). |
| Post Load Wash: | The column is washed with 2 cv of Buffer A prior to the elution cycle. Flow rate is 5 ml/min. |
| Protein Elution: | Protein is eluted from the column using a series of salt "steps". During the post load wash the TGFβ-2 fractions elute and are collected (see FIG. 3). TGFβ-1 fractions are eluted using 13% Buffer B (approximately 100 mM NaCl in buffer). The elution of the TGFβ-1 fractions is shown in FIG. 4. Following the TGFβ-1 elution 100% Buffer B is applied to the column. This removes contaminating proteins that may include BMP-3. TGFβ-1 or TGFβ-2 fractions are collected as single peaks Protein is collected from the column eluate (20 ml fractions) after 3.4 cv of the elution cycle had passed through the column. Typically, fractions number 110–120. |
| Column Regeneration: | Following the protein elution the column is first cleaned using 3 cv Buffer C. |
| Protein Pooling: | Fractions containing TGFβ-1/TGFβ-2 are identified by a combination of SDS-PAGE analysis and Western Blotting. Pooling of the fractions containing individual growth factors is then performed. |

7. Desalting Step

The final purification step for TGFβ-1/TGFβ-2 is performed using a reverse phase HPLC column. Details of the column operation are provided below. The purpose of this step is to remove the urea and salt from the Heparin Sepharose fractions by a rapid, efficient method. As in the Heparin Sepharose step TGFβ-1 and TGFβ-2 fractions are processed separately.

Figure 5:
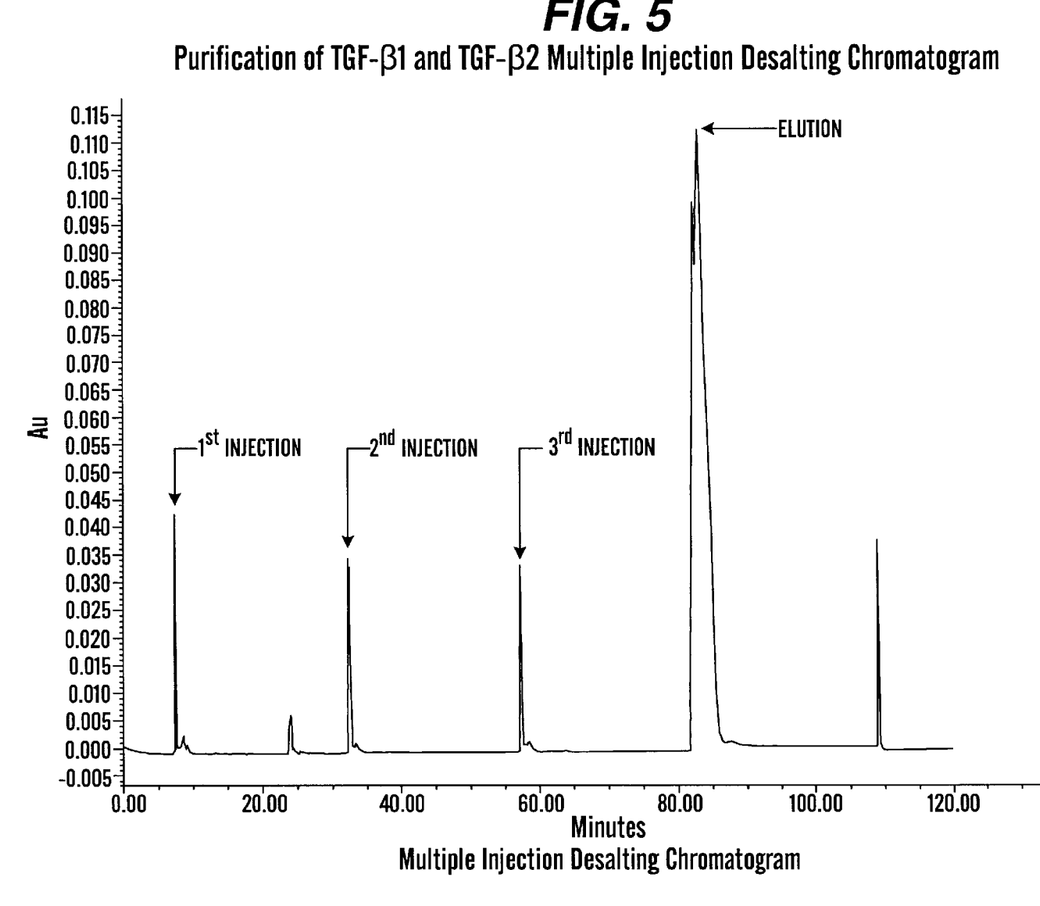
FIG. 5 shows the protein elution profile from the desalting HPLC column using the multiple injection protocol.
Figure 6:
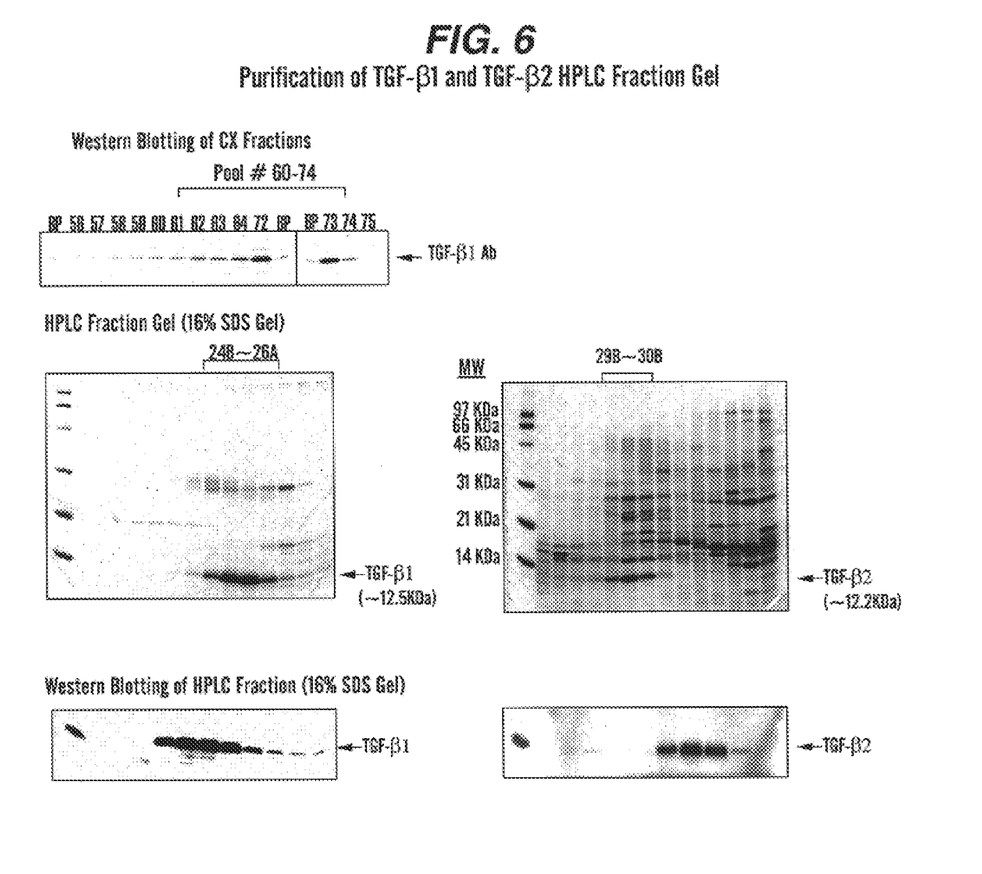
FIG. 6 shows the purification of TGF-β1 and TGF-β2 proteins by Western blot and SDS-PAGE gel analyses.
Figure 7:
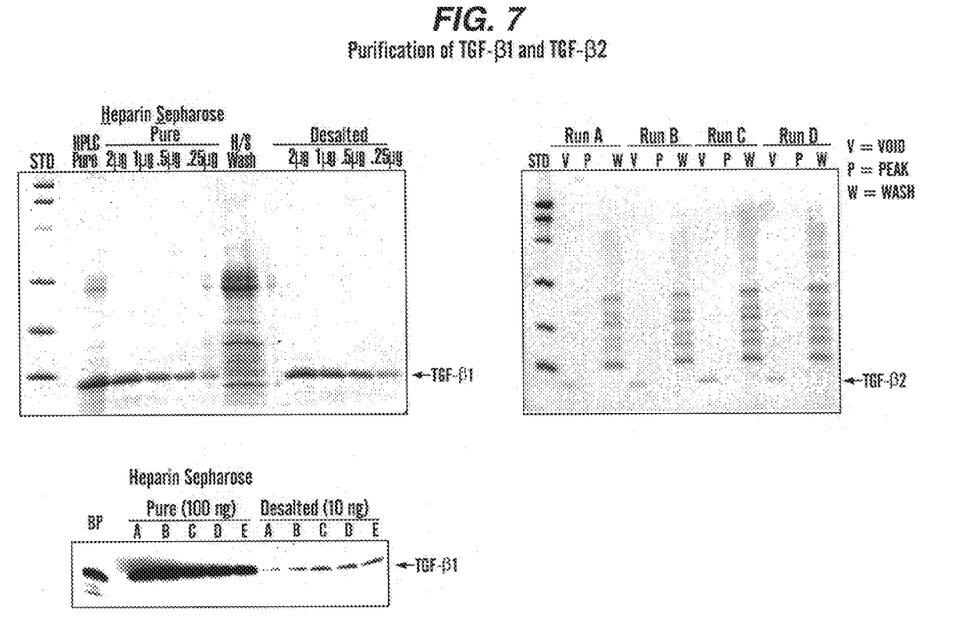
FIG. 7 shows the purification of TGF-β1 and TGF-β2 proteins following Heparin-Sepharose and desalting HPLC chromatography.

| Hardware: | |
| --- | --- |
| Column used: | Vydac 2.2 cm diameter × 25 cm height column |
| Cross Sectional Area: | Defined as $\pi r^2 = 3.8$ cm$^2$ |
| Chromatography Resin: | 10–15 $\mu$M silica beads modified with C-18 groups |
| Column Volume: | 25 cm bed height = 95 ml column |
| Controller: | Waters LC 600 HPLC system with a fraction collector |
| Column Operation: | |
| Buffers: | |
| Buffer A: | Deionized water with 0.1% trifluoroacetic acid TFA |
| Buffer B: | 90% acetonitrile ("ACN"), 9.9% deionized water with 0.1% TFA |
| Equilibration: | The column is equilibrated in 3–5 cv of Buffer A:Buffer B (98:2, or about 1.8% ACN). The flow rate is 11.4 ml/min (equivalent to 180 cm/hr). |
| Protein Load: | The Heparin Sepharose fractions are directly loaded onto the fully equilibrated column at a flow rate of 11.4 ml/min (180 cm/hr). For each loading cycle 3–5 mg of protein (in 20 ml) is loaded onto the HPLC column. Multiple injections of protein can be performed to a maximum of 20–30 mg protein. |
| Post Load Wash: | A 2 cv wash is then performed (Buffer A:Buffer B, 98:2, or about 1.8% ACN) prior to initiation of the elution cycle. (Note: where multiple injections are performed, a post load wash is performed following each injection). |
| Protein Elution: | Protein is eluted from the column using a step gradient consisting of 88% ACN (mixed from Buffers A and B described above, 2:98). The purified, desalted fractions of TGF $\beta$-1 and TGF $\beta$-2 elute within 2 cv. The elution profile is shown in FIG. 5. Individual fractions are collected and lyophilized. |
| Column Regeneration: | Following the protein elution the column is cleaned with 1–2 cv of 100% Buffer B. |
| Final Protein Pooling: | Lyophilized fractions containing TGF$\beta$-1/TGF$\beta$-2 are redissolved in 10 mM HCl at 1 mg/ml protein. SDS-PAGE analysis is used to estimate purity of the samples and Western Blotting used as a positive identification method. A typical summary of the purification is shown in Tables 1 and 2. Additional information is shown in FIGS. 6 and 7. |

TABLE 1

Purification of TGF-$\beta$1

| Process Step | Load (mg) | Pool (mg) | Extinction Coefficient | Recovery % |
| --- | --- | --- | --- | --- |
| M12 | 17200 | 14900 | 1.0 | 87 |
| CX | 14200 | 1816 | 1.0 | 13 |
| HPLC | 1450 | 39 | 2.62 | 2.7 |
| Heparin S | 39 | 22 | 2.62 | 57 |

Overall Recovery: Approximately 0.15%

TABLE 2

Purification of TGF-$\beta$2

| Process Step | Load (mg) | Pool (mg) | Extinction Coefficient | Recovery % |
| --- | --- | --- | --- | --- |
| M12 | 17200 | 14900 | 1.0 | 87 |
| CX | 14200 | 1816 | 1.0 | 13 |
| HPLC | 1450 | 43 | 2.62 | 3.0 |
| Heparin S | 43 | 22 | 2.62 | 15 |

Overall Recovery: Approximately 0.04%

While various embodiments of the present invention have been described in detail, it is apparent that modifications and adaptations of those embodiments will occur to those skilled in the art. For example, the osteoinductive factors can be used in various applications such as treating periodontal diseases and in facial reconstruction, as well as in treating other bone and joint problems. However, it is to be expressly understood that such modifications and adaptations are within the spirit and scope of the present invention, as set forth in the following claims.

What is claimed is:

1. A process for purifying TGF-$\beta$ proteins from a first solution containing demineralized bone extract, comprising:
    subjecting said first solution to filtration to obtain a second solution containing proteins having a desired range of molecular weights;
    loading said second solution onto an anion exchange resin;
    collecting the void volume from loading said second solution onto said anion exchange resin;
    loading said void volume onto a cation exchange resin;
    eluting a protein fraction from said cation exchange resin with a gradient eluant to obtain a cation exchanged fraction eluate;
    loading said cation exchanged fraction eluate onto a reverse phase HPLC column; and
    eluting a protein fraction from said HPLC column to obtain a HPLC fraction eluate enriched in a TGF-$\beta$ protein.

2. The process, as claimed in claim 1, further comprising the steps of loading said HPLC fraction eluate onto a Heparin-Sepharose column; and eluting a protein fraction from said Heparin-Sepharose column to obtain an Heparin-Sepharose eluate enriched in a TGF-$\beta$ protein.

3. The process, as claimed in claim 2, further comprising the step of loading said Heparin-Sepharose eluate onto a reverse phase HPLC column.

4. The process, as claimed in claim 1, wherein said filtration comprises:
(i) subjecting said first solution to filtration using a filtration membrane having a nominal molecular weight cut off of approximately 100 kD to produce a filtrate; and
(ii) subjecting said filtrate to filtration using a filtration membrane having a nominal molecular weight cut off of approximately 10 kD to produce a retentate as said second solution.

5. The process, as claimed in claim 1, wherein the conductivity of said second solution is adjusted to a conductivity of less than about 1,300 mhos ($1.3 \times 10^{-3}$ S) prior to loading onto said anion exchange resin.

6. The process, as claimed in claim 1, wherein the conductivity of said void is in a range from about 900 mhos ($0.9 \times 10^{-3}$ S) to about 1300 mhos ($1.3 \times 10^{-3}$ S).

7. The process, as claimed in claim 1, wherein said cation exchange eluant has a conductivity from about 1500 mhos ($1.5 \times 10^{-3}$ S) to about 40,000 mhos ($4.0 \times 10^{-2}$ S).

8. The process, as claimed in claim 1, further comprising the step of dialyzing said cation enchanged fraction eluate into deionized water using a 3.5 kD molecular weight cut off dialysis membranes.

9. The process, as claimed in claim 1, wherein said step of eluting a protein fraction from said HPLC column to obtain a HPLC fraction eluate comprises eluting a protein fraction from said HPLC column with a second eluant having a gradient of increasing acetonitrile concentration ranging from about 25 percent by volume to about 70 percent by volume to obtain a purified protein mixture.

10. The process, as claimed in claim 9, wherein said gradient of increasing acetonitrile concentration of said second eluant increases from about 29 percent by volume to about 55 percent by volume.

11. The process, as claimed in claim 9, wherein said step of eluting a protein fraction from said HPLC column comprises collecting aliquots eluting at approximately 35 to 37 percent by volume acetonitrile to produce a TGF-$\beta$1 fraction.

12. The process, as claimed in claim 9, wherein said step of eluting a protein fraction from said HPLC column comprises collecting aliquots eluting at approximately 38 to 40 percent by volume acetonitrile to produce a TGF-$\beta$2 fraction.

13. The process, as claimed in claim 9, wherein said HPLC column comprises either a plastic or hydrocarbon-modified silica packing.

14. The process, as claimed in claim 13, wherein said silica is modified by the addition of $C_4$ through $C_{18}$ hydrocarbons.

15. The process, as claimed in claim 9, wherein said HPLC column comprises a packing material selected from the group consisting of $C_4$, $C_8$ or $C_{18}$ material.

16. The process, as claimed in claim 1, wherein said anion exchange resin comprises quaternary amine functional groups.

17. The process, as claimed in claim 1, wherein said cation exchange resin comprises sulfonic acid functional groups.

18. The process, as claimed in claim 1, wherein the pH of said second solution is from about pH 8 to about pH 9 prior to said step of loading said second solution onto said anion exchange resin.

19. The process, as claimed in claim 1, wherein the pH of said void volume is from about pH 8.0 to about pH 9.0 prior to said step of loading said void volume onto said cation exchange resin.

20. The process, as claimed in claim 1, wherein said second solution, said void volume and said cation exchanged fraction eluate comprise an effective amount of urea to maintain proteins therein in solution.

21. The process, as claimed in claim 1, wherein said cation exchange loading solution has a counterion concentration less than about 0.01 M NaCl.

22. The process, as claimed in claim 1, wherein said first eluant has a counterion concentration in a range from about 0.01 M NaCl to about 0.6 M NaCl.

23. The process, as claimed in claim 1, wherein said HPLC fraction eluate comprises from about 0.05 percent by volume to about 0.15 percent by volume trifluoracetic acid.

24. The process, as claimed in claim 1, wherein said first solution containing demineralized bone extract is prepared by extracting proteins from cleaned, crushed demineralized bone particles using a compound selected from the group consisting of guanidine and urea.

25. A process for purifying TGF-$\beta$ proteins from a first solution containing demineralized bone extract, comprising:
i subjecting said first solution to filtration to obtain a second solution containing proteins having a nominal molecular weight cut off of between approximately 10 kD and approximately 100 kD;
ii adjusting the conductivity of said second solution, if necessary, to a conductivity of less than about 1,300 $\mu$mhos ($1.3 \times 10^{-3}$ S) prior to loading onto said anion exchange resin
iii loading said second solution onto an anion exchange resin;
iv collecting the void volume from loading said second solution onto said anion exchange resin;
v wherein the conductivity of said void volume is in a range from about 900 $\mu$mhos ($0.9 \times 10^{-3}$ S) to about 1300 $\mu$mhos ($1.3 \times 10^{-3}$ S);
vi loading said void volume onto a cation exchange resin;
vii eluting a protein fraction from said cation exchange resin with a first eluant having a sodium chlorine concentration of about 10 mM to about 600 mM to obtain a cation exchanged fraction eluate, having a sodium chloride concentration of about 400 to about 550 mM NaCl;
vi loading said cation exchanged fraction eluate onto a reverse phase HPLC column; and
vii eluting a protein fraction from said HPLC column with a second eluant having a gradient of increasing acetonitrile concentration ranging from about 25 percent by volume to about 70 percent by volume to obtain a purified protein mixture to obtain a HPLC fraction eluate enriched in a TGF-$\beta$ protein.

26. The process, as claimed in claim 25, wherein said step of eluting a protein fraction from said HPLC column comprises collecting aliquots eluting at approximately 35–37 percent by volume acetonitrile to produce a TGF-$\beta$1 fraction.

27. The process, as claimed in claim 25, wherein said step of eluting a protein fraction from said HPLC column comprises collecting aliquots eluting at approximately 38–40 percent by volume acetonitrile to produce a TGF-$\beta$2 fraction.

28. A process for purifying TGF-$\beta$ proteins from a first solution containing demineralized bone extract, comprising:
i subjecting said first solution to filtration to obtain a second solution containing proteins having a nominal molecular weight cut off of between approximately 10 kD and approximately 100 kD;

ii adjusting the conductivity of said second solution, if necessary, to a conductivity of less than about 1,300 µmhos ($1.3 \times 10^{-3}$ S) prior to loading onto said anion exchange resin iii loading said second solution onto an anion exchange resin comprising quaternary amine functional groups;

iv collecting the void volume from loading said second solution onto said anion exchange resin;

v wherein the conductivity of said void volume is in a range from about 900 µmhos ($0.9 \times 10^{-3}$ S) to about 1300 µmhos ($1.3 \times 10^{-3}$ S);

vi loading said void volume onto a cation exchange resin comprising sulfonic acid functional groups;

vii eluting a protein fraction from said cation exchange resin with a first eluant having a sodium chlorine concentration of about 10 mM to about 600 mM to obtain a cation exchanged fraction eluate, having a sodium chloride concentration of about 400 to about 550 mM NaCl;

viii loading said cation exchanged fraction eluate onto a reverse phase HPLC column comprising $C_4$ through $C_{18}$ hydrocarbon-modified silica packing;

ix eluting a protein fraction from said HPLC column with a second eluant having a gradient of increasing acetonitrile concentration ranging from about 25 percent by volume to about 70 percent by volume to obtain a purified protein mixture;

x collecting aliquots eluting from said HPLC column at approximately 35–37 percent by volume acetonitrile to produce a TGF-β1 fraction; and xi collecting aliquots eluting from said HPLC column at approximately 38–40 percent by volume acetonitrile to produce a TGF-β2 fraction.

* * * * *